US00PP20665P2

(12) United States Plant Patent
Trucks

(10) Patent No.: US PP20,665 P2
(45) Date of Patent: Jan. 19, 2010

(54) ***PANICUM* PLANT NAMED 'THUNDERCLOUD'**

(50) Latin Name: *Panicum virgatum*
Varietal Denomination: Thundercloud

(76) Inventor: Gary M Trucks, Amber Wave Gardens, 1460 Hillandale Rd., Benton Harbor, MI (US) 49022-9761

( * ) Notice: Subject to any disclaimer, the term of this patent is extended or adjusted under 35 U.S.C. 154(b) by 0 days.

(21) Appl. No.: 12/221,085

(22) Filed: Jul. 30, 2008

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para

(57) ABSTRACT

A new and distinct cultivar of ornamental *Panicum virgatum* plant named 'Thundercloud' with erect culms producing broad bluish foliage, with light airy panicles that persist well into the winter suitable as a potted plant, for the garden, and for cut flower arrangements.

2 Drawing Sheets

Botanical classification: *Panicum virgatum.*
Variety denomination: 'Thundercloud'.

SUMMARY, BACKGROUND AND ORIGIN OF THE PLANT

*Panicum virgatum* 'Thundercloud', hereinafter also referred to as 'Thundercloud' and "the plant" is a new and distinct cultivar of Switch Grass. It was a cross by Gary M. Trucks in 2002 between *Panicum* 'Cloud Nine' (not patented)×*Panicum virgatum* 'Northwind' (not patented) at a nursery in Benton Harbor, Mich. and selected for further observation in 2003. The plant has been successfully asexually propagated by division at the same perennial plant nursery in Benton Harbor, Mich. and found to produce identical plants that maintain the unique characteristics of the original plant. The plant is stable and reproduces true to type in successive generations of asexual reproduction.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
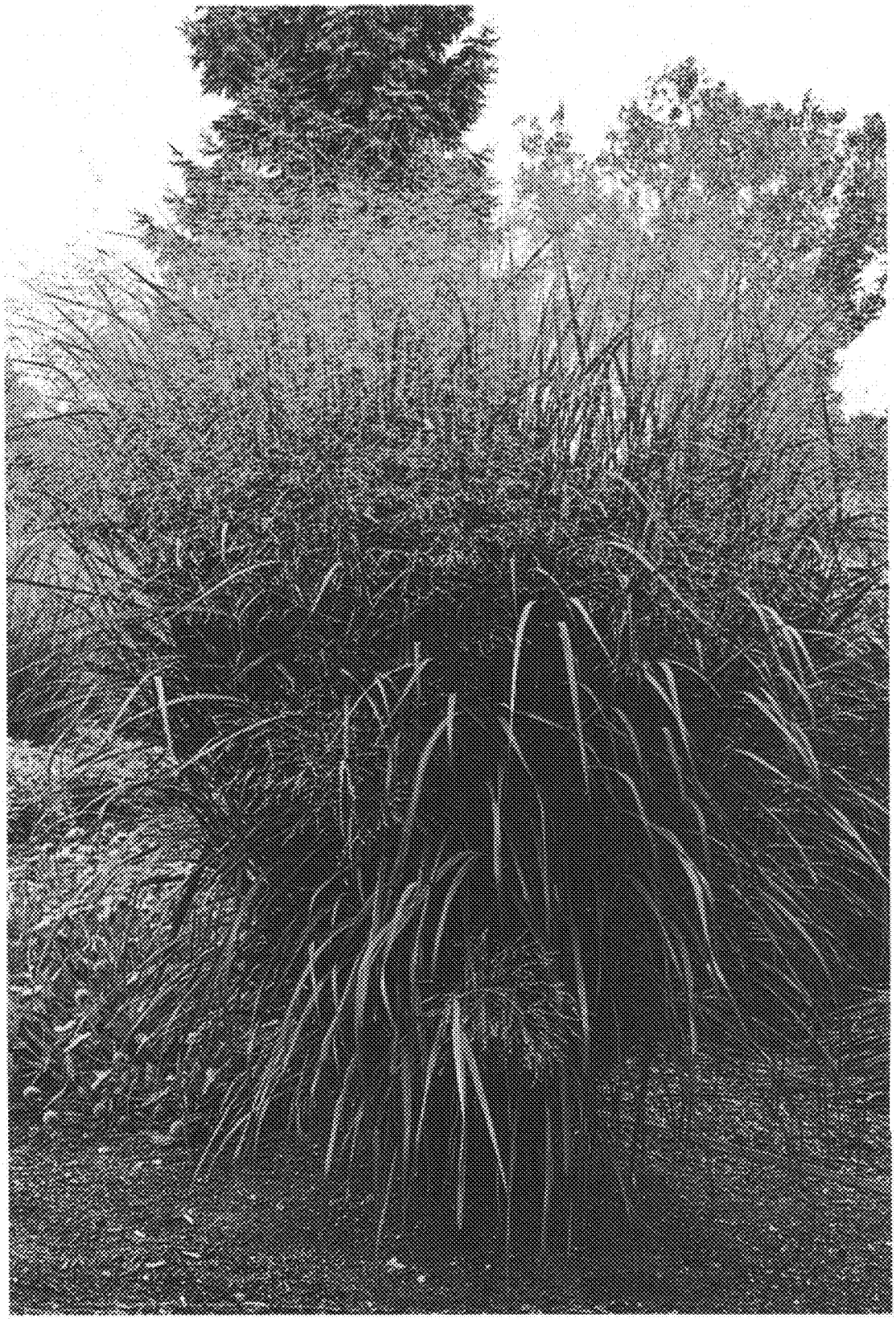
FIG. 1 shows the overall plant habit in mid-season.
Figure 2:
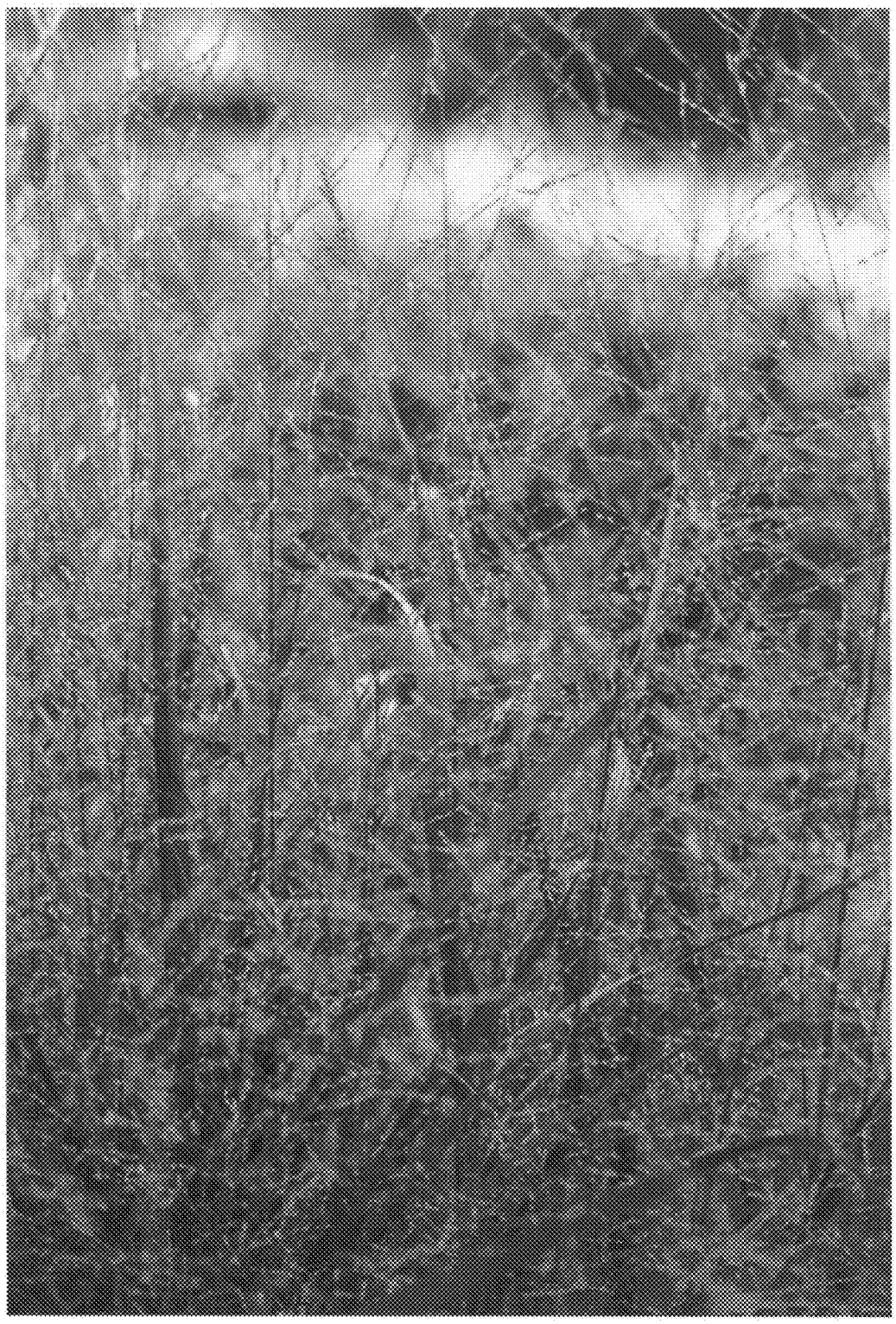
FIG. 2 shows the inflorescence in mid-July.

*Panicum virgatum* 'Thundercloud' differs from its parents as well as all other *Panicum* known to the applicant in the following traits:

1. Foliage is wider and more blue-colored.
2. Tall dense clumps with more vase-shaped habit.
3. Flower is more open and on sturdy non-floppy culms beginning in mid July and persisting well into winter.

The nearest comparison varieties are 'Dallas Blues' U.S. Plant Pat. No. 11,202, 'RR1' U.S. Plant Pat. No. 17,944 and 'Heavy Metal' (not patented). 'Thundercloud' has a much more open flower than either 'Dallas Blues' or 'Heavy Metal'.

'Thundercloud' is taller than 'Dallas Blues' which is taller than 'Heavy Metal'. 'RR1' is much shorter and has more red pigment in the foliage.

DETAILED BOTANICAL DESCRIPTION

The following descriptions and color references are based on the 2001 edition of The Royal Horticultural Society Colour Chart except where common dictionary terms are used. The new plant, 'Thundercloud', has not been observed under all possible environments. The phenotype may vary slightly with different environmental conditions, such as temperature, light, fertility, moisture and maturity levels, but without any change in the genotype. The following observations and size descriptions are of a three-year old plant in a trail garden in Zeeland, Mich. in full sun with supplemental water and fertilizer.

Parentage: Controlled cross of *Panicum virgatum* 'Cloud Nine'×*Panicum virgatum* 'Northwind'.

Propagation method: By division of the culms or tissue culture.

Time to finishing in a 4 liter pot: About three months.

Rooting habit: Normal, coarsely branching.

Plant description:

*Plant shape and habit.*—Hardy herbaceous perennial forming tightly rhizomatous clump, with upright culms topped with finely textured airy inflorescence.

*Plant size.*—Foliage height at flowering is 200 to 250 cm tall from soil line to the top of the leaves, average about 210 cm; to 45 to 50 cm wide at soil line and 200 to 245 cm at widest point just below flowers.

*Foliage description.*—Glabrous, glaucous, entire, flat, alternate, erect to arching toward tips, leaf sheath completely surrounding culm from node to almost point of attachment at ligule, linear, deciduous but persist through winter.

*Foliage size.*—65 to 95 cm long, averaging 80 cm; 1.5 to 2.0 cm wide at widest portion.

*Top surface.*—Closest to RHS N138A.

*Underside surface.*—Closest to RHS N138A.

*Veins.*—Parallel; color same as the surrounding leaf on both the top and bottom of the leaf including the central vein.

Culm (stem): Erect, cylindrical, glaucous, with about 7 to 8 leaves, 90% enclosed by leaf sheath, 140 to 160 cm long excluding panicle, about 8.0 mm wide at base; internode length 18 to 26 cm; RHS 187A to RHS N187A near nodes and where receiving full sun exposure, RHS 137B with a slight glaucous bloom on older growth; younger growth about RHS 146B.

Flower description: In finely branched open panicle, one panicle per culm, numerous spikelets per panicle, persists through winter. No fragrance detected.

*Panicle.*—Loosely pyramidal, 35 to 40 cm long, 25 to 30 cm wide; RHS 138B.

*Spikelet.*—About 8 mm long and 3 mm wide.

*Glumes.*—First glume shorter than spikelet, between RHS 187B and RHS 187C on tips and lighter than RHS 148D at base.

*Stigma.*—Two, about 3 mm long, RHS 187A.

*Anther.*—About 3 mm long, nearest RHS 173B.

Fruit: Caryopsis; 2 to 3 mm long and 1.5 mm wide, nearest RHS 164C.

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other Switch Grasses has not been observed.

I claim:

1. A new and distinct cultivar of *Panicum virgatum* plant named 'Thundercloud' as herein described and illustrated, with erect culms producing broad bluish foliage, with light airy panicles that persist well into the winter suitable as a potted plant, for the garden, and for cut flower arrangements.

* * * * *